United States Patent
Fritzler et al.

(10) Patent No.: US 11,361,929 B2
(45) Date of Patent: Jun. 14, 2022

(54) X-RAY TUBE

(71) Applicant: Siemens Healthcare GmbH, Erlangen (DE)

(72) Inventors: Anja Fritzler, Erlangen (DE); Joerg Freudenberger, Kalchreuth (DE); Marcus Radicke, Veitsbronn (DE); Peter Geithner, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/891,509

(22) Filed: Jun. 3, 2020

(65) Prior Publication Data

US 2020/0395187 A1 Dec. 17, 2020

(30) Foreign Application Priority Data

Jun. 11, 2019 (EP) .................................... 19179314

(51) Int. Cl.
*H01J 35/08* (2006.01)
*A61B 6/00* (2006.01)

(52) U.S. Cl.
CPC ............ *H01J 35/08* (2013.01); *H01J 35/112* (2019.05); *H01J 35/116* (2019.05); *A61B 6/40* (2013.01); *A61B 6/502* (2013.01); *H01J 2235/088* (2013.01)

(58) Field of Classification Search
CPC ... H01J 35/112; H01J 35/116; H01J 2235/088
See application file for complete search history.

(56) References Cited

U.S. PATENT DOCUMENTS

| | | | |
|---|---|---|---|
| 6,487,272 B1 | 11/2002 | Kutsuzawa | |
| 7,203,283 B1* | 4/2007 | Puusaari | H01J 35/08 378/143 |
| 2004/0120463 A1* | 6/2004 | Wilson | H01J 35/10 378/144 |
| 2004/0136499 A1* | 7/2004 | Holland | H01J 35/10 378/119 |

(Continued)

FOREIGN PATENT DOCUMENTS

| | | |
|---|---|---|
| DE | 2719609 A1 | 11/1978 |
| EP | 3629361 A1 | 4/2020 |

OTHER PUBLICATIONS

European Search Report for European Application No. 19179314.0 dated Jan. 17, 2020.

(Continued)

*Primary Examiner* — Chih-Cheng Kao
(74) *Attorney, Agent, or Firm* — Harness, Dickey & Pierce, P.L.C.

(57) ABSTRACT

An x-ray tube includes an electron emitter to emit an electron beam; and a multilayer anode including a first anode layer facing the electron beam and a second anode layer facing away from the electron beam. The first anode layer includes a first anode material to generate a braking radiation via the electron beam and the second anode layer includes a second anode material to generate a further x-ray radiation via the braking radiation. The further x-ray radiation is relatively more monochromatic than the braking radiation and wherein the first anode layer and the second anode layer adjoin in a planar manner.

21 Claims, 2 Drawing Sheets

(56) References Cited

U.S. PATENT DOCUMENTS

| | | | |
|---|---|---|---|
| 2008/0084966 A1* | 4/2008 | Aoki | H01J 35/24 |
| | | | 378/140 |
| 2016/0268094 A1* | 9/2016 | Yun | H01J 35/106 |
| 2016/0300686 A1* | 10/2016 | Dalakos | H01J 35/12 |
| 2018/0261350 A1* | 9/2018 | Yun | G21K 1/025 |
| 2019/0030363 A1 | 1/2019 | Silver | |
| 2019/0252149 A1* | 8/2019 | Silver | H01J 35/112 |
| 2020/0098538 A1 | 3/2020 | Fritzler et al. | |

OTHER PUBLICATIONS

European Search Report for European Application No. 19179314.0 dated Dec. 11, 2019.

\* cited by examiner

X-RAY TUBE

PRIORITY STATEMENT

The present application hereby claims priority under 35 U.S.C. § 119 to European patent application number EP 19179314.0 filed Jun. 11, 2019, the entire contents of which are hereby incorporated herein by reference.

FIELD

Embodiments of the invention generally relate to an x-ray tube, an x-ray device and a mammography device.

BACKGROUND

An x-ray tube is usually used for an imaging examination with x-ray radiation. An x-ray device typically has the x-ray tube and an x-ray detector for carrying out the imaging examination. The imaging examination can be in particular an imaging mammography examination, in particular a mammography screening. Ideally the x-ray tube enables the imaging examination with a high image quality and equally with as low an x-ray radiation dose as possible, preferably by adapting an emission spectrum of the x-ray radiation. The x-ray radiation or the emission spectrum, in particular the energy distribution thereof, is preferably matched with respect to a maximum image contrast. In this regard it is known that the x-ray radiation dose is so much lower, the more monochromatic the x-ray radiation or the emission spectrum.

For instance, conventional x-ray radiation is adjusted by way of a filter, wherein equally the image quality and the x-ray radiation dose should be optimized. The filter usually reduces the x-ray radiation which is useful for the image quality, as a result of which to compensate an intensity of the x-ray radiation has to be increased. One further possibility of adjusting the emission spectrum is to vary the anode material generating the x-ray radiation.

The as yet unpublished application EP 18196848.8 discloses an x-ray tube with a surface structure of the anode which alternates periodically at least in sections. US 2019/0 030 363 A1 discloses two anode materials which are distanced from one another, wherein the first anode material generates braking radiation and the second anode material emits monochromatic x-ray radiation by way of the braking radiation.

SUMMARY

Embodiments of the invention are directed to an x-ray tube, an x-ray device and a mammography device, in which a portion of monochromatic x-ray radiation is increased.

Advantageous embodiments are described in the claims.

In at least one embodiment, the inventive x-ray tube comprises:
 an electron emitter emitting an electron beam and
 a multilayer anode,
 wherein the multilayer anode has a first anode layer facing the electron beam and a second anode layer facing away from the electron beam,
 wherein the first anode layer has a first anode material for generating a braking radiation by way of the impinging electron beam,
 wherein the second anode layer has a second anode material for generating a further x-ray radiation by way of the braking radiation,
 wherein the further x-ray radiation is more monochromatic than the braking radiation and
 wherein the first anode layer and the second anode layer adjoin one another in a planar manner.

In at least one embodiment, the inventive x-ray tube comprises:
 an electron emitter to emit an electron beam; and
 a multilayer anode including a first anode layer facing the electron beam and a second anode layer facing away from the electron beam, the first anode layer including a first anode material to generate a braking radiation via the electron beam and the second anode layer including a second anode material to generate a further x-ray radiation via the braking radiation,
 wherein the further x-ray radiation is relatively more monochromatic than the braking radiation and wherein the first anode layer and the second anode layer adjoin in a planar manner.

At least one embodiment is directed to an x-ray device, comprising:
 the x-ray tube of claim 1; and
 an x-ray detector.

At least one embodiment is directed to a mammography device, comprising:
 the x-ray device of claim 9; and
 a chest support apparatus.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The x-ray tube of at least one embodiment is in particular advantageous because, on account of the spatial proximity of the first anode layer to the second anode layer, more braking radiation penetrates the second anode layer, as a result of which a portion of monochromatic x-ray radiation is preferably increased in the emission spectrum of the x-ray tube. In other words, less braking radiation gets lost outside of the second anode material. A further advantage may be that the second anode layer is preferably not affected by primary electrons, but instead by secondary electrons. An image quality and/or an x-ray radiation dose can preferably be optimized during an imaging examination of a patient. For instance, the imaging examination can comprise an imaging mammography examination, a fluoroscopy, an angiography, a computed tomography and/or a contrast agent-assisted examination.

The x-ray tube can be embodied in particular according to a stationary anode x-ray tube, a rotary anode x-ray tube or a rotary piston x-ray tube. The x-ray tube is typically evacuated. The electron beam typically has a number of electrons, which are preferably accelerated from the electron emitter to the multi-layer anode. The electron beam is directed for instance from a deflection unit, in particular from a magnetic deflection unit, of the x-ray tube at the multi-layer anode. The electron emitter can in particular have a coil emitter, a flat emitter or a field effect emitter.

The multi-layer anode has in particular a number of anode layers of different anode materials. The first anode layer can differ from the second anode layer in terms of extent and/or volume and/or weight. The first anode layer can be applied to the second anode layer or vice versa, for instance. The application can comprise in particular spraying, casting, fastening, vaporizing, sputtering, selective electrochemical coating and/or masking.

It is basically conceivable that after application the first anode layer and/or the second anode layer is removed again at least partially, particularly if the application takes place without masking. By way of the application, the first anode layer and the second anode layer adjoin one another in a planar manner. There is typically no material and/or no distance between the first anode layer and the second anode layer.

The first anode layer and the second anode layer share in particular a common planar contact area. The common planar contact area can be deformed to be two-dimensional, for instance flat or three-dimensional, for instance in a wavelike, L- or U-shape. If the common planar contact area is deformed to be three-dimensional, the first anode layer at least partially encloses in particular the second anode layer or vice versa. According to a particular embodiment, the second anode layer encloses the first anode layer, in particular in an L- or U-shape, because as a result more braking radiation can impinge on the second anode layer.

The fact that the first anode layer is facing the electron beam and that the second anode layer is facing away from the electron beam means in particular that the electron beam preferably firstly impinges on the first anode layer. The primary electrons of the electron beam preferably impinge on the first anode layer.

The primary electrons are preferably such electrons which have not yet interacted with the first anode material or the second anode material. Electrons which have already carried out an interaction with the first anode material or the second anode material are typically secondary electrons. The interaction can be a scattering, a fluorescing, a deflection, an absorption and/or a weakening.

The electron beam is typically absorbed and/or weakened completely or at least partially by the first anode layer. If the electron beam is partially absorbed, the electron beam downstream of the first anode layer can basically impinge on the second anode layer. The first anode layer is arranged in particular between the electron emitter and the second anode layer. The multi-layer anode is preferably aligned relative to the electron beam such that the electron beam firstly impinges on the first anode layer.

The first anode layer can include, in particular, the first anode material. The first anode material is embodied in particular so that the braking radiation can be generated from the impinging electrons. Generation of the braking radiation typically takes place by way of an interaction of an impinging electron of this type with a nucleus of the first anode material, in that the impinging electron deflects and is thus weakened by a Delta energy, wherein a photon with the Delta energy is produced as part of the braking radiation. The braking radiation is typically a wideband and/or continuous x-ray radiation.

The second anode layer can include, in particular, the second anode material. The second anode material can be in particular a converter material. The second anode material is embodied in particular such that the further x-ray radiation can be generated from the braking radiation absorbed by the second anode material.

The generation of the further x-ray radiation can take place in particular by a fluorescing of the second anode material as a function of an impinging braking radiation photon. Alternatively or in addition electrons back-scattered by the first anode material, in particular the secondary electrons, can strike the second anode material, wherein the further x-ray radiation is generated by fluorescing, for instance. The further x-ray radiation can have in particular the fluorescence photons. A fluorescence rate of the second anode material is typically higher than a fluorescence rate of the first anode material.

In an embodiment, the first anode material differs in particular from the second anode material in that the further x-ray radiation is more monochromatic than the braking radiation. The first anode material is especially preferably suited to generating electrons from the braking radiation and the second anode material is especially preferably suited to generating the further x-ray radiation from the braking radiation. The fact that the further x-ray radiation is more monochromatic than the braking radiation means in particular that an emission spectrum of the braking radiation is more wideband compared with an emission spectrum of the further x-ray radiation.

If the further x-ray radiation is more monochromatic, the emission spectrum of the further x-ray radiation is typically characterized by a higher portion of characteristic x-ray radiation, in particular by a higher portion of photons of the K lines of the second anode material compared with the emission spectrum of the braking radiation. The emission spectrum of the further x-ray radiation can in particular have more and/or stronger characteristic lines than the emission spectrum of the braking radiation.

One embodiment provides that the first anode material in a characteristic line of an emission spectrum differs from the second anode material. In this respect this embodiment is advantageous because the first anode material can be optimized to generate the braking radiation and the second anode material can be optimized to generate the further x-ray radiation.

One embodiment provides that the first anode material has at least one material from the following list:
tungsten,
gold.

This embodiment is advantageous because tungsten is particularly heat-resistant and/or gold has a particularly advantageous emission spectrum.

One embodiment provides that the second anode material has at least one material from the following list:
tin,
silver,
molybdenum,
palladium.

This embodiment is particularly advantageous because an emission spectrum with a specific mixture of the preferred material has a characteristic line in the energy range between 20 to 34 keV, which can be advantageous in particular for an imaging mammography examination. Further mixtures of the materials are basically conceivable, which typically differ in the respective emission spectrum, in particular in the characteristic lines thereof.

One embodiment provides that the first anode layer together with the second anode layer forms an anode microstructure, wherein the anode microstructure is arranged in a periodically recurring manner along a surface of the multilayer anode and wherein the electron beam impinges on the surface at an angle of incidence of less than 90°. The electron beam impinges on the surface at an acute angle in particular. The angle of incidence can amount in particular to between 10° and 60°, preferably between 20° and 50° and/or particularly advantageously 45°. The angle of incidence is typically an angle between the electron beam and a, in particular macroscopic, surface of the multilayer anode. The angle of incidence is in particular independent of the arrangement and/or embodiment of the anode microstructure.

The anode microstructure can be conical, in particular if an individual anode microstructure of the periodically recurring anode microstructure is shown sectionally. Viewed macroscopically, the individual anode microstructure typically forms a channel or a wave. In particular, the periodically recurring anode microstructure forms a wavelike or sinusoidal surface of the multilayer anode. In other words, the surface of the multilayer anode is typically channeled.

The anode microstructure can have, for example, a maximum extent of less than 1 mm, preferably of less than 100 μm, particularly advantageously of less than 10 μm. The maximum extent can correspond to a height of the cone, for instance. The fact that the anode microstructure is arranged so as to recur periodically means in particular that the anode microstructure is replicated repeatedly along the surface. The number of anode microstructures which recur periodically form in particular the wavelike or sinusoidal surface of the multilayer anode.

This embodiment is particularly advantageous because the electron beam and/or the braking radiation and/or the further x-ray radiation, particularly before exiting through an x-ray radiation outlet window, can interact repeatedly with the multilayer anode, preferably with the periodically recurring anode microstructure.

In this embodiment, a portion of monochromatic x-ray radiation is preferably increased by the periodically recurring anode microstructure. A further advantage may be that electrons scattered back onto a cone of the anode microstructure strike a further cone of the anode microstructure in order to generate the further x-ray radiation. In other words, the portion of monochromatic x-ray radiation is increased in that the multilayer anode has a number of cones, in particular anode layers, with the second anode material for generating the further x-ray radiation.

A further advantage may be that the surface of the multilayer anode facing the electron beam, in particular of the first anode material, is enlarged.

One embodiment provides that the multilayer anode has a third anode layer facing the electron beam and a fourth anode layer facing away from the electron beam, wherein the third anode layer has a third anode material for generating the braking radiation by way of the impinging electron beam, wherein the fourth anode layer has a fourth anode material for generating the further x-ray radiation by way of the braking radiation, wherein the third anode layer and the fourth anode layer adjoin one another in a planner manner and wherein the second anode material in a characteristic line of an emission spectrum differs from the fourth anode material.

The third anode layer and the fourth anode layer are arranged in particular adjacent to the first anode layer and the second anode layer relative to the electron beam. The second anode material and the fourth anode material can essentially have the same materials and typically differ in a mixture of the materials.

Alternatively it is conceivable for the second anode material to have a material which does not have the fourth anode material and vice versa. Basically the second anode material can have partially the same characteristic lines as the fourth anode material. The first anode material can correspond to the third anode material or alternatively in a characteristic line can differ from the third anode material. This embodiment is in particular advantageous because the multilayer anode can provide an emission spectrum with a number of characteristic lines.

The x-ray tube can therefore preferably be used for different imaging examinations.

A particularly advantageous embodiment of the preceding embodiment is that the electron beam is directed at the first anode layer or at the third anode layer. This embodiment is particularly advantageous because the multilayer anode can provide different emission spectra. For instance, in this case an imaging examination can be carried out with further x-ray radiation of the second anode layer or with further x-ray radiation of the fourth anode layer. Alternatively or in addition, according to a dual energy measuring protocol, the energy spectrum can be defined alternatively during the imaging measurement in particular by directing the electron beam at the first anode layer or at the third anode layer.

One embodiment provides that the anode microstructure, in particular as described previously, is arranged in a periodically recurring manner and a first cone of the anode microstructure has the first anode layer and the second anode layer, and a second cone of the anode microstructure has the third anode layer and the fourth anode layer. In this respect, this embodiment is advantageous because an x-ray tube is provided with a compact multilayer anode, which preferably generates different emission spectra.

An x-ray device has the x-ray tube and an x-ray detector. The x-ray detector can in particular detect the further x-ray radiation after x-raying the patient. A medical image of the patient can preferably be reconstructed and/or provided in a storage unit and/or on a display unit by way of the detected further x-ray radiation.

The mammography device has in particular the x-ray device and a chest support apparatus. A chest of the patient, for instance a female patient, can preferably be supported on the chest support apparatus during the imaging mammography examination.

The invention is described and explained in more detail below on the basis of the example embodiments shown in the Figures. In principle, structures and units which remain the same are identified in the following description of the figures with the same reference signs as in the first occurrence of the relevant structure or unit.

Figure 1:
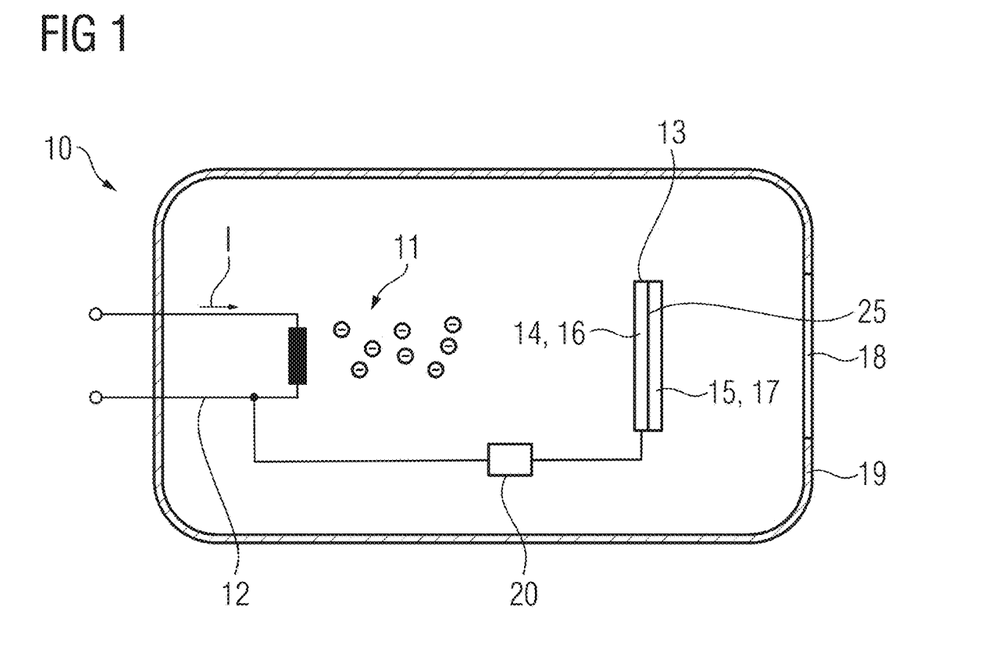
FIG. 1 shows an x-ray tube in a first example embodiment.

FIG. 1 shows an x-ray tube 10 in a first example embodiment. The x-ray tube 10 has an electron emitter 12 emitting an electron beam 11 and a multilayer anode 13. The electron emitter 12 emits the electron beam 11 in particular during an imaging examination as a function of a heating current I. The electrons of the electron beam 11 are in particular accelerated by a voltage supply 20 toward the multilayer anode 13. The acceleration voltage typically lies between 20 and 150 keV.

The multilayer anode 13 has a first anode layer 14 facing the electron beam 11 and a second anode layer 15 facing away from the electron beam 11. The first anode layer 14 and the second anode layer 15 adjoin one another in a planar manner. In this example embodiment, a common, planar contact area 25 is two-dimensional, in particular flat.

The first anode layer 14 has a first anode material 16 for generating a braking radiation by way of the impinging electron beam 11. The first anode material 16 has for instance at least one material from the following list:
tungsten,
gold.

The second anode layer 15 has a second anode material 17 for generating a further x-ray radiation by way of the braking radiation. The first anode material 16 differs in particular from the second anode material 17 in a characteristic line of an emission spectrum. The second anode material 17 has for instance at least one material from the following list:
tin,
silver,
molybdenum,
palladium.

The further x-ray radiation is more monochromatic than the braking radiation. The further x-ray radiation can pass through an x-ray radiation exit window 18 out of a housing 19 of the x-ray tube 10, for instance. There is typically a vacuum within the housing 19.

Figure 2:
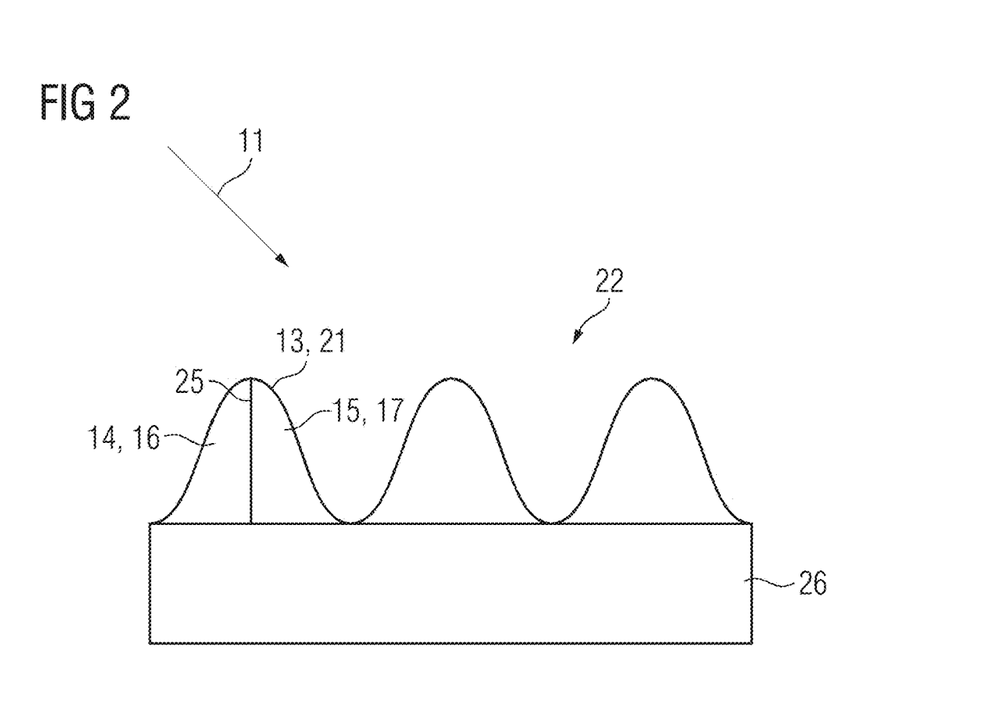
FIG. 2 shows a multi-layer anode in a second example embodiment.

FIG. 2 shows the multilayer anode 13 in a second example embodiment. In this example embodiment the electron beam 11 is identified with an arrow.

The first anode layer 14, together with the second anode layer 15, forms an anode microstructure 21. The anode microstructure 21 is arranged in a periodically recurring manner along a surface 22 of the multilayer anode 13. The anode microstructure 21 is conical, when viewed individually sectionally. The periodically recurring anode microstructures are preferably arranged adjacent to one another so that the first anode material 16 and the second anode material 17 alternate.

The electron beam 11 impinges on the surface 22 at an angle of incidence of less than 90°. The surface 22 is wave-like and/or sinusoidal. A lower side 26 of the surface 22 of the multilayer anode 13 typically has tungsten or an alternative heat-resistant and/or heat-conductive cooling material. The electrons of the electron beam 11 preferably strike the first anode layer 14 and the second anode layer 15 to a lesser extent or not at all.

Figure 3:
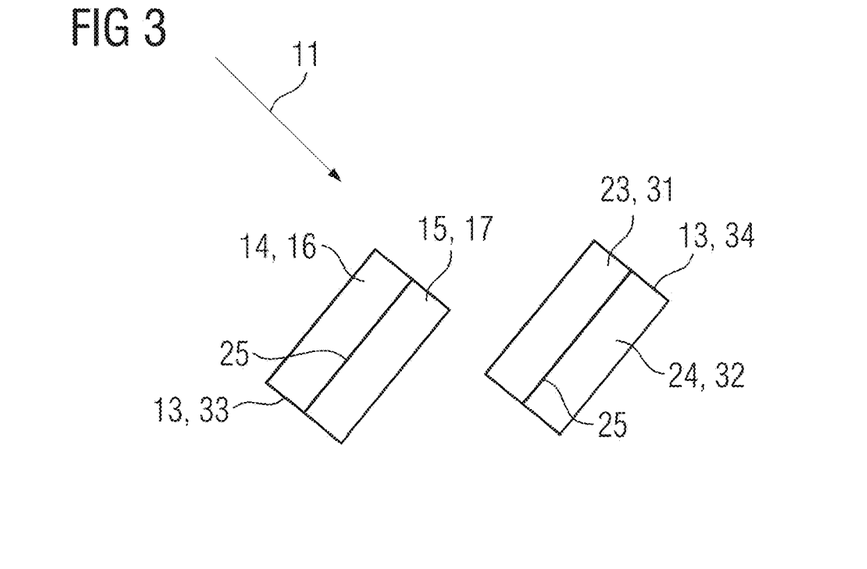
FIG. 3 shows a multilayer anode in a third example embodiment.

FIG. 3 shows the multilayer anode 13 in a third example embodiment.

The multilayer anode 13 has a third anode layer 23 facing the electron beam 11 and a fourth anode layer 24 facing away from the electron beam 11. The third anode layer 23 has a third anode material 31 for generating the braking radiation by way of the impinging electron beam 11. The fourth anode layer 24 has a fourth anode material 32 for generating the further x-ray radiation by way of the braking radiation.

The third anode layer 23 and the fourth anode layer 24 adjoin one another in a planar manner. The second anode material 17 differs from the fourth anode material 32 in a characteristic line of an emission spectrum.

Compared with the example embodiment shown in FIG. 2, the first anode layer 14 and the second anode layer 15 form a first anode micro structure 33 and the third anode layer 23 and the fourth anode layer 24 form a second anode microstructure 34. A wavelike surface, in particular with periodically recurring anode microstructures with different emission spectra, can essentially result typically independently of whether the first anode microstructure 33 and/or the second anode microstructure 34 is embodied in the shape of a cone or rectangle.

In this example embodiment the first anode layer 14, the second anode layer 15, the third anode layer 23 and the fourth anode layer 24 are at an angle of approx. 90° with respect to the electron beam, wherein the angle of incidence of the electron beam 11 is smaller than 90° with respect to the macroscopic surface. A smaller or larger angle is basically conceivable.

Furthermore it is conceivable for the electron beam 11 to be directed at the first anode layer 14 or at the third anode layer 23, for instance by way of a magnetic deflection unit of the x-ray tube 10. In this case, the braking radiation and the associated further x-ray radiation is generated in particular mostly, preferably by more than 75%, particularly advantageously more than 95%, either by the first anode microstructure 33 or by the second anode microstructure 34.

Figure 4:
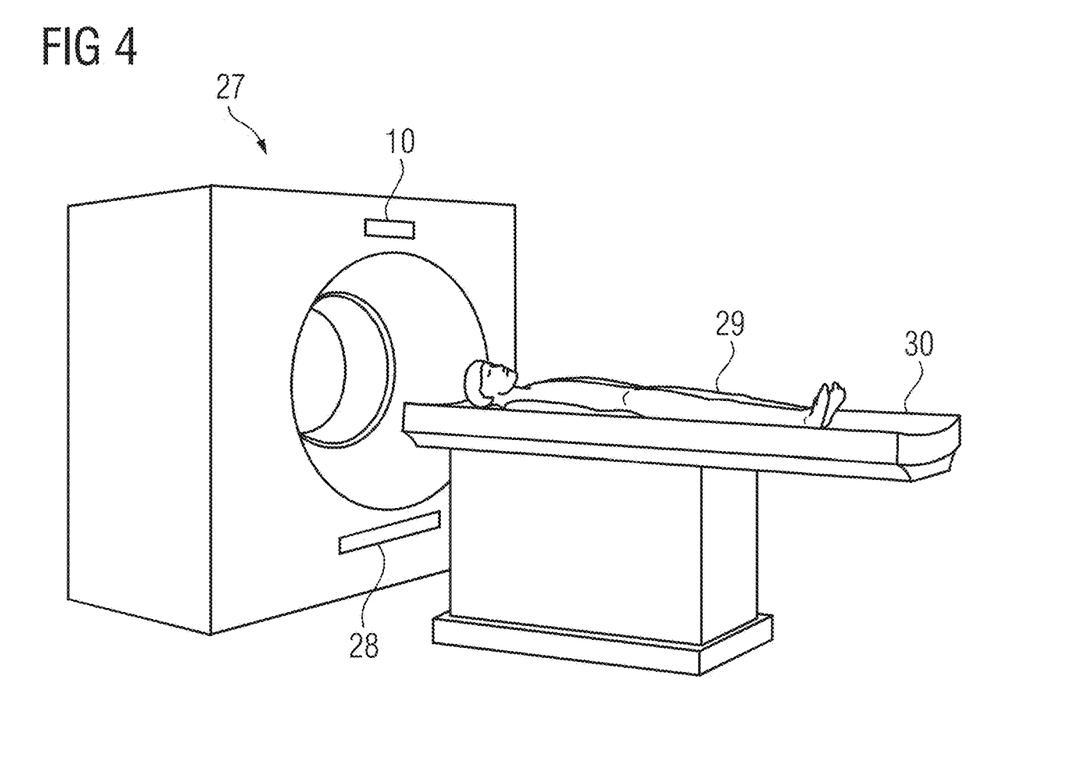
FIG. 4 shows an x-ray device in a fourth example embodiment.

FIG. 4 shows an x-ray device 27 in a fourth example embodiment. The x-ray device 27 has the x-ray tube 10 and an x-ray detector 28. A patient 29 is supported on a patient couch 30. In this example embodiment the x-ray device 27 is embodied as a computed tomography device. Alternatively, the x-ray device 27 can be part of a mammography device or a C-arm angiography system.

Although the invention has been illustrated and described in detail using the preferred example embodiments, the invention is still not limited by the disclosed examples, and a person skilled in the art can derive other variations therefrom that are still covered by the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An x-ray tube, comprising:
   an electron emitter to emit an electron beam;
   a lower surface structure; and
   a multilayer anode on the lower surface structure, the multilayer anode including a first anode layer facing the electron beam and a second anode layer facing away from the electron beam, the first anode layer including a first anode material to generate a braking radiation via the electron beam and the second anode layer including a second anode material to generate a further x-ray radiation via the braking radiation, wherein
   the further x-ray radiation is relatively more monochromatic than the braking radiation,
   the first anode layer and the second anode layer share a common planar contact area and form an anode microstructure,
   the anode microstructure is arranged in a periodically recurring manner,
   the anode microstructure has a sinusoidal or wave structure along a surface of the multilayer anode,
   the electron beam impinges on the surface of the multilayer anode at an angle of incidence of between 10° and 60°, and
   the lower surface structure includes at least one of a heat-resistance or a heat-conductive cooling material.

2. The x-ray tube of claim 1, wherein the first anode material, in a characteristic line of an emission spectrum, differs from the second anode material.

3. The x-ray tube of claim 1, wherein the electron beam impinges on the surface of the multilayer anode at an angle of incidence of between 20° and 50°.

4. The x-ray tube of claim 1, wherein the electron beam impinges on the surface of the multilayer anode at an angle of incidence of about 45°.

5. The x-ray tube of claim 1, wherein the common planar contact area is at an angle of less than 90 degrees with respect to a surface of the lower surface structure.

6. The x-ray tube of claim 1, wherein the at least one of a heat-resistance or a heat-conductive cooling material includes tungsten.

7. The x-ray tube of claim 1, wherein the first anode material includes at least one of tungsten or gold.

8. The x-ray tube of claim 2, wherein the first anode material includes at least one of tungsten or gold.

9. The x-ray tube of claim 1, wherein the second anode material includes at least one of tin, silver, molybdenum, or palladium.

10. The x-ray tube of claim 2, wherein the second anode material includes at least one of tin, silver, molybdenum, or palladium.

11. The x-ray tube of claim 7, wherein the second anode material includes at least one of tin, silver, molybdenum, or palladium.

12. The x-ray tube of claim 8, wherein the second anode material includes at least one of tin, silver, molybdenum, or palladium.

13. The x-ray tube of claim 1, wherein
   the multilayer anode includes a third anode layer facing the electron beam and a fourth anode layer facing away from the electron beam,
   the third anode layer includes a third anode material to generate the braking radiation via the electron beam,
   the fourth anode layer includes a fourth anode material to generate the further x-ray radiation via the braking radiation,
   the third anode layer and the fourth anode layer adjoin in a planar manner, and
   the second anode material, in a characteristic line of an emission spectrum, differs from the fourth anode material.

14. The x-ray tube of claim 13, wherein the electron beam is directed at the first anode layer or at the third anode layer.

15. The x-ray tube of claim 2, wherein
   the multilayer anode includes a third anode layer facing the electron beam and a fourth anode layer facing away from the electron beam,
   the third anode layer includes a third anode material to generate the braking radiation via the electron beam,
   the fourth anode layer includes a fourth anode material to generate the further x-ray radiation via the braking radiation,
   the third anode layer and the fourth anode layer adjoin in a planar manner, and the second anode material, in the characteristic line of the emission spectrum, differs from the fourth anode material.

16. The x-ray tube of claim 15, wherein the electron beam is directed at the first anode layer or at the third anode layer.

17. An x-ray device, comprising:
the x-ray tube of claim 1; and
an x-ray detector.

18. A mammography device, comprising:
the x-ray device of claim 17; and
a chest support apparatus.

19. An x-ray device, comprising:
the x-ray tube of claim 2; and
an x-ray detector.

20. A mammography device, comprising:
the x-ray device of claim 19; and
a chest support apparatus.

21. An x-ray tube, comprising:
an emitter configured to emit an electron beam; and
a multilayer anode including a first anode layer and a second anode layer, the first anode layer facing the emitter and including a first anode material to generate electromagnetic radiation based on the electron beam, and the second anode layer facing away from the emitter and including a second anode material to generate x-ray radiation based on the electromagnetic radiation, wherein
the x-ray radiation is more monochromatic than the electromagnetic radiation,
the first anode layer and the second anode layer form an anode microstructure, which is arranged in a periodically recurring manner,
the anode microstructure has a sinusoidal or wave structure along a surface of the multilayer anode,
the multilayer anode is configured such that the electron beam impinges on the surface of the multilayer anode at an angle of incidence of between 10° and 60°, and
a planar surface of the first anode layer is adjoined to a planar surface of the second anode layer.

* * * * *